United States Patent
Hwang et al.

(10) Patent No.: US 11,213,208 B2
(45) Date of Patent: Jan. 4, 2022

(54) MULTISPECTRAL IMAGING DEVICE

(71) Applicant: DAEGU GYEONGBUK INSTITUTE OF SCIENCE AND TECHNOLOGY, Daegu (KR)

(72) Inventors: Jae Youn Hwang, Daegu (KR); Jae Eun Jang, Daegu (KR); Man Jae Kim, Gyeonggi-do (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 618 days.

(21) Appl. No.: 16/082,812

(22) PCT Filed: Mar. 7, 2017

(86) PCT No.: PCT/KR2017/002423
§ 371 (c)(1),
(2) Date: Sep. 6, 2018

(87) PCT Pub. No.: WO2017/155265
PCT Pub. Date: Sep. 14, 2017

(65) Prior Publication Data
US 2019/0090751 A1 Mar. 28, 2019

(30) Foreign Application Priority Data
Mar. 7, 2016 (KR) .................. 10-2016-0027156

(51) Int. Cl.
*A61B 5/00* (2006.01)
*F21V 5/04* (2006.01)
(Continued)

(52) U.S. Cl.
CPC .............. *A61B 5/0077* (2013.01); *A61B 5/00* (2013.01); *A61B 5/0033* (2013.01); *A61B 5/441* (2013.01);
(Continued)

(58) Field of Classification Search
CPC ....... A61B 5/0077; A61B 5/00; A61B 5/0033; A61B 5/441; A61B 5/6898;
(Continued)

(56) References Cited

U.S. PATENT DOCUMENTS

| | | | |
|---|---|---|---|
| 8,888,286 B2 * | 11/2014 | Grenon | A61B 3/1005 351/206 |
| 2005/0265585 A1 * | 12/2005 | Rowe | G06K 9/00046 382/124 |

(Continued)

FOREIGN PATENT DOCUMENTS

| | | |
|---|---|---|
| JP | 2008-129446 A | 6/2008 |
| KR | 10-2006-0111906 A | 10/2006 |

(Continued)

OTHER PUBLICATIONS

International Search Report (and English translation) and Written Opinion of the International Searching Authority for PCT/KR2017/002423 dated Jun. 12, 2017.

*Primary Examiner* — Sanjay Cattungal
(74) *Attorney, Agent, or Firm* — Hauptman Ham, LLP

(57) ABSTRACT

A multispectral imaging device in accordance with one embodiment comprises: an illumination unit for emitting LED lighting to the skin for skin illumination; and a detection unit for causing light reflected from the skin to be incident on a camera, wherein the illumination unit is arranged on the outer side of the detection unit, so that a path of the LED lighting emitted from the illumination unit is formed on the outer side of the detection unit, and a path of the light reflected from the skin is formed on the inner side of the detection unit.

17 Claims, 8 Drawing Sheets

(51) Int. Cl.
*F21V 9/00* (2018.01)
*F21S 2/00* (2016.01)

(52) U.S. Cl.
CPC .............. *F21S 2/005* (2013.01); *F21V 5/04* (2013.01); *F21V 9/00* (2013.01); *A61B 5/6898* (2013.01); *A61B 2562/0233* (2013.01)

(58) Field of Classification Search
CPC .... A61B 2562/0233; F21S 2/005; F21V 5/04; F21V 9/00
See application file for complete search history.

(56) References Cited

U.S. PATENT DOCUMENTS

| | | | | |
|---|---|---|---|---|
| 2005/0265586 A1* | 12/2005 | Rowe | ................... | G06K 9/0012 382/124 |
| 2005/0271258 A1* | 12/2005 | Rowe | ................... | G06K 9/2018 382/124 |
| 2006/0152586 A1* | 7/2006 | Komiya | ................... | G01J 3/50 348/207.99 |
| 2006/0251408 A1* | 11/2006 | Konno | ................... | G01J 3/0291 396/14 |
| 2008/0298649 A1* | 12/2008 | Ennis | ................... | G06K 9/0012 382/125 |
| 2011/0163163 A1* | 7/2011 | Rowe | ................... | G06K 9/2018 235/462.25 |
| 2011/0304705 A1* | 12/2011 | Kantor | ................. | A61B 5/0059 348/49 |
| 2015/0164327 A1* | 6/2015 | Yaroslavsky | ......... | A61B 5/4872 600/476 |
| 2015/0205992 A1* | 7/2015 | Rowe | ................... | G06K 9/2018 382/124 |
| 2017/0079530 A1* | 3/2017 | DiMaio | ................. | G06T 7/0012 |
| 2017/0245792 A1* | 8/2017 | Tversky | ............... | A61B 5/0075 |
| 2017/0367580 A1* | 12/2017 | DiMaio | ................. | A61B 5/0064 |
| 2018/0143073 A1* | 5/2018 | Goldring | ............ | G01N 21/3563 |
| 2018/0184972 A1* | 7/2018 | Carmi | .................... | G01J 3/0256 |
| 2020/0288982 A1* | 9/2020 | Islam | ..................... | G01N 21/35 |

FOREIGN PATENT DOCUMENTS

| | | |
|---|---|---|
| KR | 10-0781235 B1 | 11/2007 |
| KR | 10-0853655 B1 | 8/2008 |
| KR | 10-1214440 B1 | 12/2012 |
| KR | 10-2015-0018973 A | 2/2015 |
| KR | 10-1533840 B1 | 7/2015 |
| KR | 20-2015-0003564 U | 10/2015 |
| WO | 2015/013288 A2 | 1/2015 |

* cited by examiner

MULTISPECTRAL IMAGING DEVICE

CROSS REFERENCE TO RELATED APPLICATIONS

This application is a national stage filing under section 371 of International Application No. PCT/KR2017/002423, filed on Mar. 7, 2017, and published on Sep. 14, 2017 as WO 2017/155265, which claims priority to Korean Patent Application No. 10-2016-0027156, filed on Mar. 7, 2016. The entire contents of WO2017/155265 are hereby incorporated herein by reference.

TECHNICAL FIELD

The present invention relates to a multispectral imaging device and, more particularly, to a multispectral imaging device that may emit light having a small bandwidth in consecutive wavelength bands and be detachably attached irrespective of a type of a mobile device.

BACKGROUND ART

Generally, in order to verify a skin condition or detect a skin ailment, a patient may visit a hospital or a skin care shop for a thorough examination using a skin diagnosing device. The skin diagnosing device used in the hospital or the skin care shop may be manipulated by a doctor or an expert. Also, the doctor may confirm a diagnosis based on a result acquired from the skin diagnosing device. Thus, it is difficult for the patient to perform the diagnosis using the skin diagnosis device by himself or herself.

Among various skin diagnosing devices, devices having a spectral imaging function may have a higher diagnostic accuracy than a typical skin diagnosing device and be capable of performing a quantitative analysis. However, most of the devices may be large in size and expensive and thus, unsuitable for use in home.

To solve this, there has been developed a multispectral imaging device small-sized to be carried by a user and detachably attached to a mobile device. A typical multispectral imaging device may perform multispectral imaging by rotating an optical filter wheel using a small motor and changing an optical filter. In a case of using a motor, an image acquisition speed of the multispectral imaging may be low and there is a limit in reducing a size, which may reduce the portability.

Also, a skin diagnosing device without the multispectral imaging function such as a wood lamp may be used to detect the skin disease or perform the skin diagnosis. The wood lamp may be based on a principle that when an ultraviolet ray is irradiated to the skin, different colors appear based on a sebum, a sensitivity, and a keratin condition of the skin. The wood lamp may be used to check a condition of the skin that can not be seen with the naked eye and thus, help to make proper skin care in accordance with a type of skin.

However, the wood lamp may have a low portability and represent the skin condition using only colors on a screen, which makes it difficult for a non-specialist user to accurately diagnose the current skin condition.

DISCLOSURE OF INVENTION

Technical Goals

An aspect provides a multispectral imaging device that has a high portability, is easy to use, and allows a user to easily verify a current skin condition.

Another aspect provides a multispectral imaging device configured to be attachable and detachable irrespective of a shape of a mobile device.

Still another aspect provides a multispectral imaging device that acquires an image of a predetermined wavelength band by selectively lighting on or off a light emitting diode (LED) light source without need to rotate an LED substrate.

Yet another aspect provides a multispectral imaging device that acquires an image with increased clarity by blocking external light and light reflected from a skin without interacting with the skin.

Further another aspect provides a multispectral imaging device in which a path of LED light emitted from an illuminator is formed to be different from a path of light reflected or scattered by a skin.

Still another aspect provides a multispectral imaging device used to check a skin hydration and a skin disease such as seborrheic dermatitis.

Technical Solutions

According to an aspect, there is provided a multispectral imaging device including an illuminator configured to emit light emitting diode (LED) light for skin illumination to a skin and a detector configured to allow light reflected from the skin to be incident on a camera, wherein the illuminator is disposed on an outer side of the detector such that a path of the LED light emitted from the illuminator is formed externally to the detector and a path of the light reflected from the skin is formed internally to the detector.

The detector may include an optical lens configured to refract the light reflected from the skin and a first polarizing plate configured to polarize the light refracted by the optical lens in a first direction, and the camera may be disposed on a center axis of the first polarizing plate and the optical lens.

The detector may further include a shield configured to internally receive the optical lens and the first polarizing plate, and the illuminator may be disposed on an outer side of the shield.

The illuminator may include an LED substrate on which a plurality of LED light sources is mounted and a plurality of band-pass filters provided to be in contact with at least a portion of the plurality of LED light sources, and the LED substrate may be in a ring shape.

The plurality of LED light sources may include one ultraviolet (UV) LED, one near infrared (NIR) LED, and a plurality of white LEDs or a plurality of LEDs having different wavelengths corresponding to a center wavelength of the plurality of band-pass filters, and the plurality of band-pass filters may be arranged to be in contact with the plurality of white LEDs or the plurality of LEDs.

A number of the band-pass filters may be less than a number of the white LEDs by one.

The plurality of LED light sources and the plurality of band-pass filters may be selectively connected by controlling the plurality of LED light sources to be on or off, and the plurality of LED light sources may be controlled to be on or off by an embedded system controlled by the mobile device.

The illuminator may further include a diffusion plate disposed to be in contact with the plurality of band-pass filters in a direction in which the LED light is promoted, to diffuse the LED light, and the diffusion plate may include a diffuser configured to diffuse light in a same shape as a shape that the plurality of LED light sources is mounted.

The illuminator may further include a second polarizing plate disposed to be in contact with the diffusion plate in the direction in which the LED light is promoted, to polarize the LED light diffused by the diffusion plate in a second direction, and the second polarizing plate may include a polarizer in a same shape as the diffuser.

The multispectral imaging device may further include a cover configured to internally receive the illuminator and the detector, wherein the cover may allow the illuminator and the detector to be disposed in a darkroom such that an external light influence corresponding to the light reflected from the skin or the LED light emitted from the illuminator is blocked.

The cover may include a connecting member used for attachment to the mobile device, and the connecting member may be adjustable in length.

According to another aspect, there is also provided a multispectral imaging device including an illuminator configured to emit LED light for skin illumination to a skin and a detector configured to allow light scattered on the skin to be incident on a camera, wherein the illuminator and the detector are arranged on a same axis, a path of the LED light emitted from the illuminator is formed to be inclined toward the skin, and a path of the light scattered or reflected by the skin is formed on the same axis.

The illuminator may include an LED substrate on which a plurality of LED light sources is mounted and a plurality of band-pass filters provided to be in contact with at least a portion of the plurality of LED light sources, the LED substrate may include an inclined plane formed to be inclined toward the skin, and the plurality of LED light sources may be mounted on the inclined plane.

The illuminator may further include a diffusion plate disposed to be in contact with the plurality of band-pass filters in a direction in which the LED light is promoted, to diffuse the LED light and a first polarizing plate disposed to be in contact with the diffusion plate in the direction in which the LED light is promoted, to polarize the LED light diffused by the diffusion plate in a first direction.

The multispectral imaging device may further include a shield provided in a cylindrical shape to internally receive the detector, wherein the shield may be configured to prevent the LED light diffused by the diffusion plate from being introduced to the path of the light scattered or reflected by the skin.

The detector may include a second polarizing plane configured to polarize the light scattered or reflected by the skin in a second direction orthogonal to the first direction, and the second polarizing plate may be configured to prevent light reflected from the skin from being incident on the camera.

The detector may further include an optical lens configured to refract the light polarized by the second polarizing plate, and the skin, the second polarizing plate, the optical lens, and the camera may be on a same line.

The LED substrate may be in a ring shape, the detector may be disposed to penetrate the LED substrate, and the plurality of LED light sources may be radially arranged on the LED substrate at intervals.

The multispectral imaging device may further include a cover configured to internally receive the illuminator and the detector, wherein the detector may be disposed on a center axis of the cover and the illuminator is spaced apart from the center axis in a radial direction.

One end of the cover may be disposed adjacent to the camera, the other end of the cover may be disposed adjacent to the skin, and the cover may have a cross-sectional area that decreases from one end toward the other end.

Effects

According to example embodiment, it is possible to provide a multispectral imaging device that has a high portability, is easy to use, and allows a user to easily verify a current skin condition.

According to example embodiment, it is possible to provide a multispectral imaging device configured to be attachable and detachable irrespective of a shape of a mobile device.

According to example embodiment, it is possible to provide a multispectral imaging device that acquires an image of a predetermined wavelength band by selectively lighting on or off a light emitting diode (LED) light source without need to rotate an LED substrate.

According to example embodiment, it is possible to provide a multispectral imaging device that acquires an image with increased clarity by blocking external light and light reflected from a skin without interacting with the skin.

According to example embodiment, it is possible to provide a multispectral imaging device in which a path of LED light emitted from an illuminator is formed to be different from a path of light reflected or scattered by a skin.

According to example embodiment, it is possible to provide a multispectral imaging device used to check a skin hydration and a skin disease such as seborrheic dermatitis.

BEST MODE FOR CARRYING OUT THE INVENTION

Figure 1:
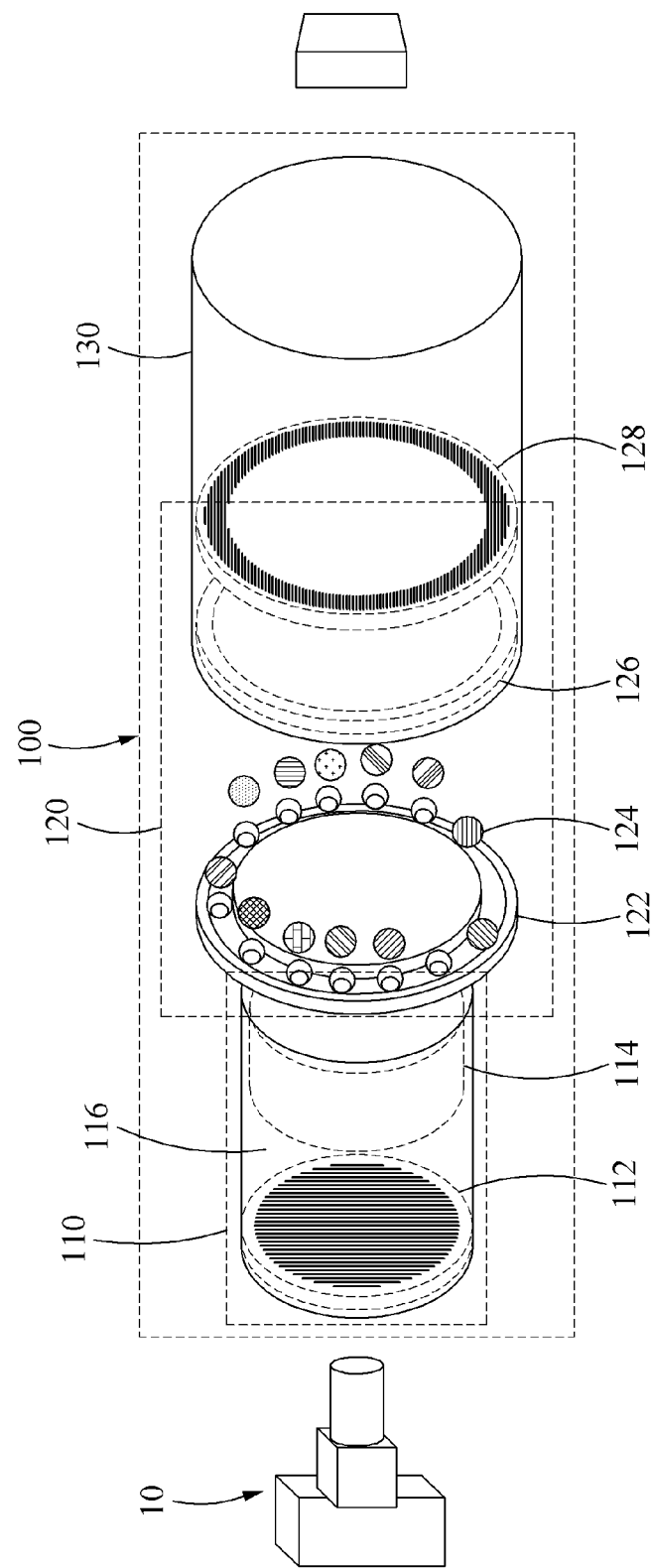
FIG. 1 is an exploded view illustrating a multispectral imaging device according to an example embodiment.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

A component described in any one of the example embodiments and a component including a common function or feature will be described using the same names in other example embodiments. Unless otherwise stated, the description in any one of the example embodiments may be applicable to other example embodiments, and a detailed description will be omitted in an overlapping range.

Figure 2:
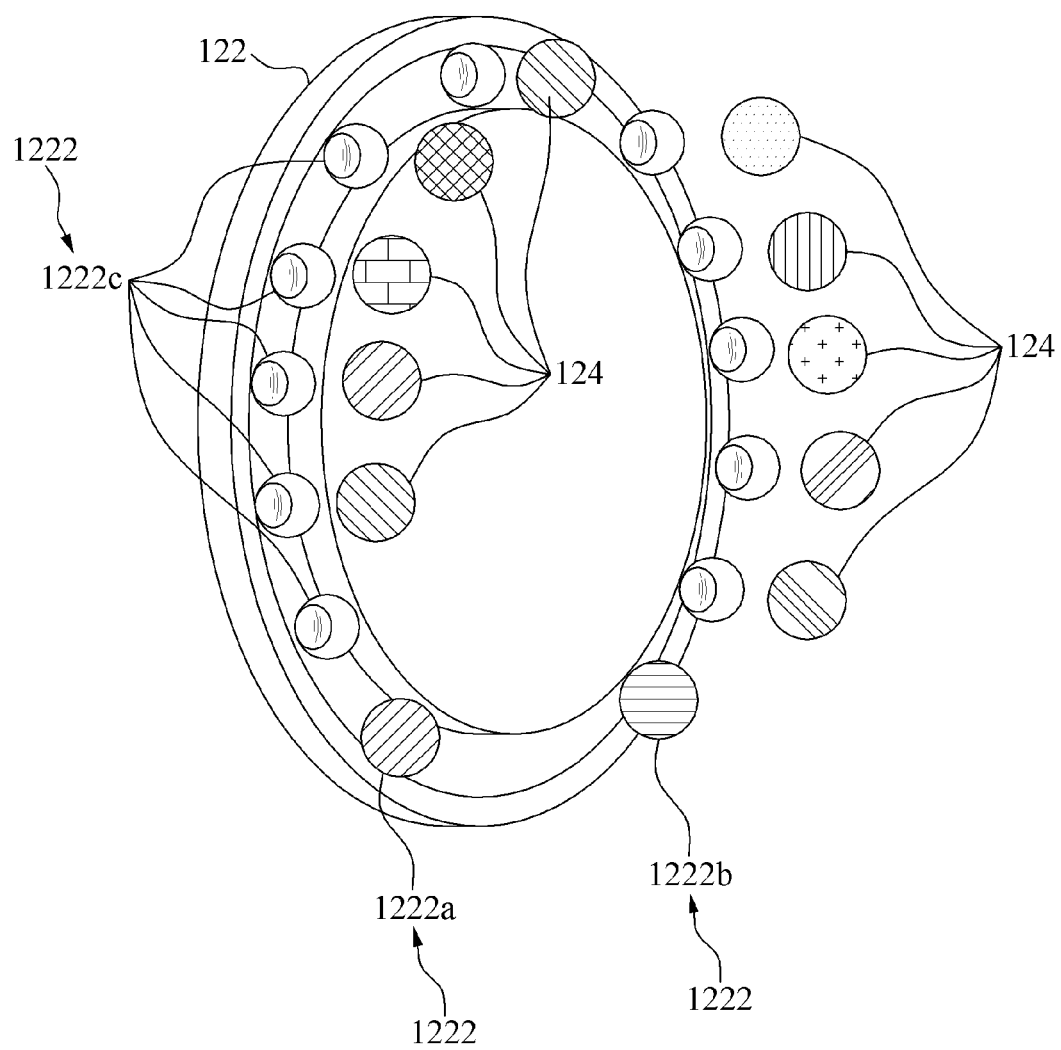
FIG. 2 is a diagram illustrating an illuminator.
Figure 3:
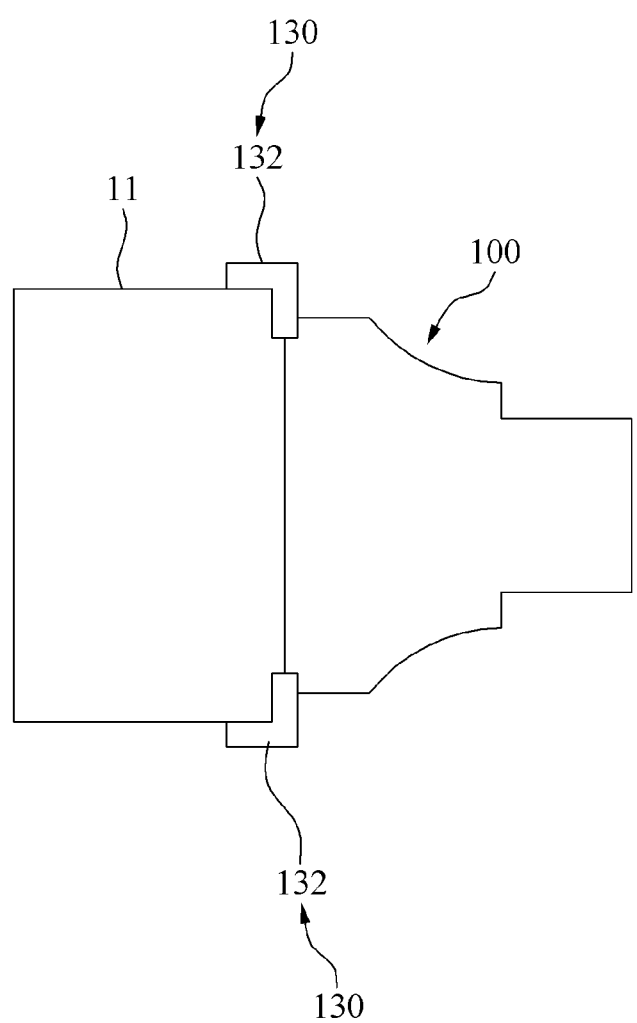
FIG. 3 is a diagram illustrating a multispectral imaging device mounted on a mobile device.

FIG. 1 is an exploded view illustrating a multispectral imaging device according to an example embodiment, FIG. 2 is a diagram illustrating an illuminator, and FIG. 3 is a diagram illustrating a multispectral imaging device mounted on a mobile device.

Referring to FIG. 1, a multispectral imaging device 100 may acquire light via one side and transfer the acquired light to a camera 10 connected to the other side. In this example, the camera 10 may be a camera of a mobile device or an independently used camera.

The multispectral imaging device 100 may include a detector 110, an illuminator 120, and a cover 130.

The detector 110 may be provided in one end of the multispectral imaging device 100 to be in contact with the camera 10. The detector 110 may include a first polarizing plate 112, an optical lens 114, and a shield 116. Also, the camera 10 may be disposed on a center axis of the optical lens 114 and the first polarizing plate 112.

The first polarizing plate 112 may polarize light having passed through the optical lens 114 to be incident on the camera 10. In this example, the first polarizing plate 112 may be configured as a vertical polarizing plate to transmit vertical light among incident light. Through this, the camera 10 may acquire light with less noise formed by, for example, unpolarized light obtained through direct reflection.

The optical lens 114 may be disposed to be in contact with the first polarizing plate 112. The optical lens 114 may be configured as a single lens or a plurality of lenses. Desirably, a focal point may be formed at a predetermined distance from a lens of the camera 10.

The optical lens 114 may allow the focal point to be formed at a predetermined position so that the multispectral imaging device 100 is readily used in various types of the camera 10.

The shield 116 may be provided outside the first polarizing plate 112 and the optical lens 114 to form a darkroom between the first polarizing plate 112 and the optical lens 114. The shield 116 may form the darkroom so that the light collected at the first polarizing plate 112 through the optical lens 114 is not affected by external light. Also, the shield 116 may prevent noise occurring when the light having passed through the optical lens 114 is reflected from the cover 130 to be incident on the camera 10 directly without passing the first polarizing plate 112.

The illuminator 120 may be disposed on an outer side of the shield 116 to be in contact with the first polarizing plate 112. The illuminator 120 may emit light for skin observation and pass the light reflected from a skin to be transferred to the first polarizing plate 112.

The illuminator 120 may include a light emitting diode (LED) substrate 122, a plurality of band-pass filters 124, a diffusion plate 126, and a second polarizing plate 128.

The LED substrate 122 may be disposed to be in contact with the optical lens 114 and attached to the optical lens 114. For example, the LED substrate 122 may be provided at a periphery of the optical lens 114 in a ring shape. The LED substrate 122 may further include a shield between the LED substrate 122 and the optical lens 114 to prevent the light from directly entering the camera 10. For brevity, the LED substrate 122 may be defined as the ring shape in the following description. However, embodiments are not limited thereto, and the LED substrate 122 may also be provided in various shapes.

Also, the LED substrate 122 may be implemented as a ring-shaped LED printed circuit board (PCB). A plurality of LED light sources may be mounted on the LED substrate 122 in a direction facing the optical lens 114. When the LED substrate 122 is attached to the optical lens 114, a shadow and distortion of the light emitted from the LED substrate 122 may be minimized.

The plurality of LED light sources may perform multispectral imaging by emitting light of various wavelengths, allow a user to directly observe a lesion site using emitted white light, and verify a skin condition using ultraviolet (UV) rays and infrared rays.

Referring to FIG. 2, a plurality of LED light sources 1222 may be mounted on one side of the LED substrate 122 to emit LED light. The plurality of LED light sources 1222 may include one the UV LED 1222a, one near infrared (NIR) LED 1222b, and white LEDs 1222c. The UV LED 1222a may emit UV LED light, the NIR LED 1222b may emit infrared LED light, and the white LEDs 1222c may emit white LED light.

The white LEDs 1222c may be replaced with a plurality of LEDs emitting LED light having different wavelengths to correspond to a center wavelength of the plurality of band-pass filters 124. The plurality of LEDs may include, for example, a blue LED that emits LED light having a wavelength of 424 nanometers (nm) or 450 nm and a green LED that emits LED light having a wavelength of 550 nm.

The plurality of band-pass filters 124 may be disposed to be in contact with the white LEDs 1222c. In this example, a number of the plurality of band-pass filters 124 may be less than a number of the white LEDs 1222c by one. When the number of the white LEDs 1222c is N, the number of the plurality of band-pass filters 124 may be N−1 such that the plurality of band-pass filters 124 changes a band of white LED light emitted from remaining white LEDs 1222c except one of the white LEDs 1222c. Also, the plurality of band-pass filters 124 may filter lights having different wavelengths in a range from 400 to 700 nm.

As described above, the plurality of band-pass filters 124 may be disposed to be in contact with the plurality of LEDs that emits LED lights having different wavelengths to correspond to a center wavelength of the plurality of band-pass filters 124. For example, a band-pass filter having a center wavelength of 424 nm or 450 nm may be disposed to be in contact with a blue LED that emits LED light having a wavelength of 424 nm or 450 nm, and a band-pass filter having a center wavelength of 550 nm may be disposed to be in contact with a green LED that emits LED light having a wavelength of 550 nm.

Also, the LED substrate 122 may be controlled by an embedded system to perform selection or combination of the plurality of band-pass filters 124. Specifically, the LED substrate 122 may perform a light-on operation on the plurality of LED light sources 1222 emitting the LED light through an external control, thereby selecting or combining filters by lighting on or lighting off the plurality of LED light sources 1222 instead of controlling a filter using a motor.

In this example, a controller for the embedded system may be provided on the LED substrate 122 but not be limited thereto. The controller may also be provided at a position that does not interfere with a path of the emitted LED light and light reflected from the skin.

The diffusion plate 126 may be disposed to be in contact with the LED substrate 122. To diffuse the LED light emitted from the plurality of LED light sources 1222, the diffusion plate 126 may include a diffuser in an area in which the LED light is output and pass the reflected light through a light passing area in which the diffuser is absent.

Because the LED light emitted from the plurality of LED light sources 1222 has a relatively small light emitting angle, the LED light may be concentrated. To prevent such light concentration, the diffusion plate 126 may diffuse the LED light to allow surface emitting of the LED light and, simultaneously, to minimize an influence of the reflected light in the emitted LED light. In this instance, since the LED substrate 122 is in the ring shape, the diffusion plate 126 or the diffuser of the diffusion plate 126 may also be in the ring shape.

The second polarizing plate 128 may be disposed to be in contact with the diffusion plate 126. To polarize the LED light diffused by the diffusion plate 126 in one direction, the second polarizing plate 128 may include a polarizer in an area in which the LED light is diffused and polarize the diffused LED light.

Since the diffuser that diffuses the LED light in the diffusion plate 126 is in the ring shape, the polarizer of the second polarizing plate 128 may also be in the ring shape. As such, the polarizer of the second polarizing plate 128 may be provided in the same shape as the diffuser of the diffusion plate 126.

Because the multispectral imaging device 100 uses the light reflected and scattered at the skin, the second polarizing plate 128 may be configured to polarize the LED light in a direction orthogonal to the first polarizing plate 112.

When the first polarizing plate 112 is a vertical polarizing plate, the second polarizing plate 128 may be a horizontal polarizing plate orthogonal to the first polarizing plate 112.

However, embodiments are not limited to the foregoing and thus, an angle between a first polarizing plate and a second polarizing plate may be adjusted based on a type of light.

In addition to the above-described shape, the LED substrate 122, the diffusion plate 124, and the second polarizing plate 128 may be formed in a shape that a path of the LED light emitted toward the skin does not intersect with a path of the light scattered or reflected by the skin to travel toward the camera.

The cover 130 may be provided outside the first polarizing plate 112, the optical lens 114, the LED substrate 122, the diffusion plate 126, and the second polarizing plate 128 to form a dark room. By forming the dark room, the cover 130 may prevent the LED light emitted from the plurality of LED light sources 1222 and the light reflected from the skin from being affected by external light. Through this, the camera 10 may acquire the light reflected from the skin with increased clarity.

Referring to FIG. 3, the cover 130 may include a connecting member on a side in contact with the camera 10.

To be easily attached to or detached from a mobile device or a device including the camera 10 such as a portable terminal, the multispectral imaging device 100 may include the connecting member 132 to be detachably attached to the corresponding device at one end of the cover 130. The connecting member 132 of the cover 130 may be formed in various types, for example, an insertion type, a hook shape, and a compression shape.

A length of the connecting member 132 may be adjusted to increase a compatibility between a mobile device 11 and the multispectral imaging device 100. In other words, a distance between the connecting member 132 and the multispectral imaging device 100 may be adjusted to adjust a position of the multispectral imaging device 100 connected to the connecting member 132. Through this, the connecting member 132 may be connected to the camera 10 irrespective of a position of the camera 10 attached to the mobile device 11.

Hereinafter, an operation of a multispectral imaging device will be further described based on the structure of FIGS. 1 through 3.

The plurality of LED light sources 1222 of the LED substrate 122 may emit LED light. In this instance, a user may use a mobile device connected to the multispectral imaging device 100 for embedded control such that LED light of the white LEDs 1222c in contact with a desired band-pass filter of the band-pass filters 124 is emitted or LED light of all the LED light sources 1222 is emitted.

The LED substrate 122 may be provided at a periphery of the optical lens 114 in the ring shape. Thus, the LED light emitted from the LED substrate 122 may be emitted in the ring shape identically to the shape of the LED substrate 122 to reach the diffusion plate 126. The LED substrate 122 may be formed in various shapes in addition to the ring shape. Hereinafter, the LED substrate 122 will be described as the ring shape for brevity, and the shape of the LED substrate 122 does not limit the scope of the present disclosure.

The emitted LED light may illuminate the skin by passing the diffusion plate 126 and the second polarizing plate 128. Because the LED light emitted in the ring shape has a relatively small light emitting angle, the LED light may be concentrated. To diffuse the concentrated light, the diffusion plate 126 may include the diffuser in an area in which the emitted LED light reaches the diffusion plate 126. Through this, the emitted LED light may be formed as a surface light source even in a distance between the diffusion plate 126 and one end of the cover 130 to illuminate the skin.

The LED light diffused by passing the diffusion plate 126 may be incident on the second polarizing plate 128. The second polarizing plate 128 may include the polarizer in an area in which the diffused LED light reaches the second polarizing plate 128 to polarize the diffused LED light. The diffused LED light may pass the polarizer of the second polarizing plate 128 and be polarized in one direction to illuminate the skin as the surface light source.

The LED light illuminating the skin may be scattered or reflected by the skin. The scattered or reflected LED light may be collected by the optical lens 114. In this instance, the scattered or reflected LED light may be incident on the optical lens 114 and refracted. The refracted LED light may be collected in the camera 10.

The scattered or reflected LED light having passed the optical lens 114 may pass the first polarizing plate 112, be polarized in one direction, and be emitted to the camera 10.

In this example, the collected LED light may include at least one of different wavelength light emitted from the plurality of LED light sources 1222, white light, a UV ray, and an infrared ray. Thus, a central processing unit (not shown) connected to the camera 10 may process the light acquired from the camera 10 to perform multispectral imaging, direct observation using the white light, and skin examination using the UV ray or the infrared ray.

The central processing unit may be included in a mobile device including a camera and may also be an electronic device connected to the camera 10 through wired or wireless communication to analyze the connected LED light.

The scattered or reflected LED light having passed the optical lens 114 may be incident on the first polarizing plate 112 instead of the camera 10 directly, due to the shield 116 provided externally to the optical lens 114 and the first polarizing plate 112.

Figure 4:
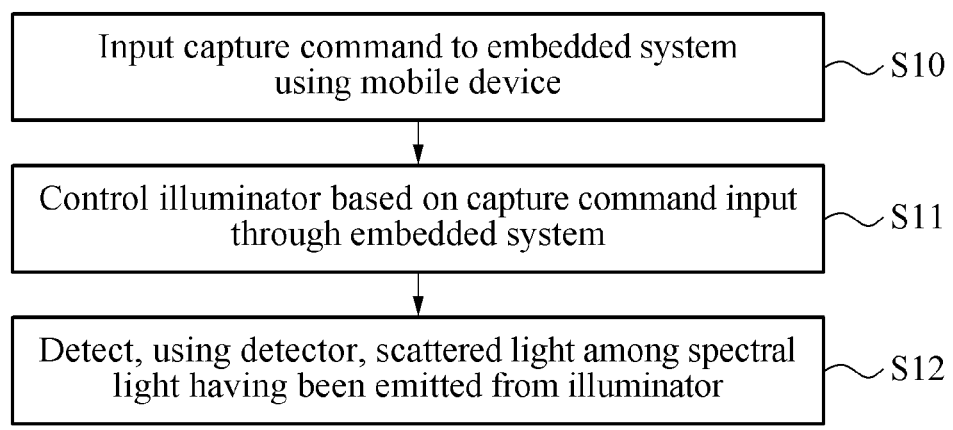
FIG. 4 is a flowchart illustrating a method of detecting light by connecting a multispectral imaging device to a mobile device and controlling a device using the mobile device.

FIG. 4 is a flowchart illustrating a method of detecting light by connecting a multispectral imaging device to a mobile device and controlling a device using the mobile device.

Referring to FIG. 4, a method of detecting light by connecting a multispectral imaging device to a mobile device and controlling a device using the mobile device may include operation S10 of inputting a capture command to an embedded system using a mobile device, operation S11 of controlling an illuminator, for example, a plurality of LED light sources based on the capture command input through the embedded system, and operation S12 of detecting, by a detector, scattered light among the spectral light having been emitted from the illuminator.

In operation S10, a user may input the capture command to the embedded system using the mobile device. The multispectral imaging device may include the embedded system and thus, may receive the capture command from an external source through wired or wireless communication.

The capture command input to the embedded system may be output from, for example, an application installed in the mobile device. However, embodiments are not limited thereto, and the capture command may be input to the embedded system using various methods.

In operation S11, the embedded system may control the illuminator based on the input capture command. The embedded system may control the illuminator based on the capture command acquired in operation S10. As described above, the illuminator may include an LED substrate on which a plurality of LED light sources is mounted and a plurality of band-pass filters. Since the plurality of LED light sources includes an UV LED and an NIR LED, the illuminator may set an LED for emitting light by controlling the embedded system.

The plurality of band-pass filters may be provided on a path of the LED light emitted from the plurality of LED light sources to obtain light of a predetermined wavelength band from the LED light. Among the plurality of LED light sources, the embedded system may selectively light on an LED from which spectral light of a desired wavelength band is to be obtained, thereby controlling the illuminator based on the capture command.

In operation S12, the mobile device may detect scattered light among the spectral light having been emitted from the illuminator using the detector. The spectral light having been emitted from the illuminator may be emitted to the skin through the diffusion plate and the second polarizing plate to be used for skin illumination. Also, the light scattered on the skin may be incident on the camera of the mobile device by passing through the optical lens and the first polarizing plate. In this example, the first polarizing plate and the second polarizing plate may be provided to polarize the light in directions orthogonal to each other.

The light incident on the camera of the mobile device may be analyzed using, for example, an application installed in the mobile device. An analysis result may be provided to a user in a form of, for example, text, picture, or image.

The multispectral imaging device may have a high portability, be easy to use, and allow a user to easily verify a current skin condition. Also, the multispectral imaging device may be detachably attached to the mobile device irrespective of a shape of the mobile device.

The description of the multispectral imaging device is provided with the foregoing examples. Hereinafter, another example of the multispectral imaging device will be described.

Figure 5:
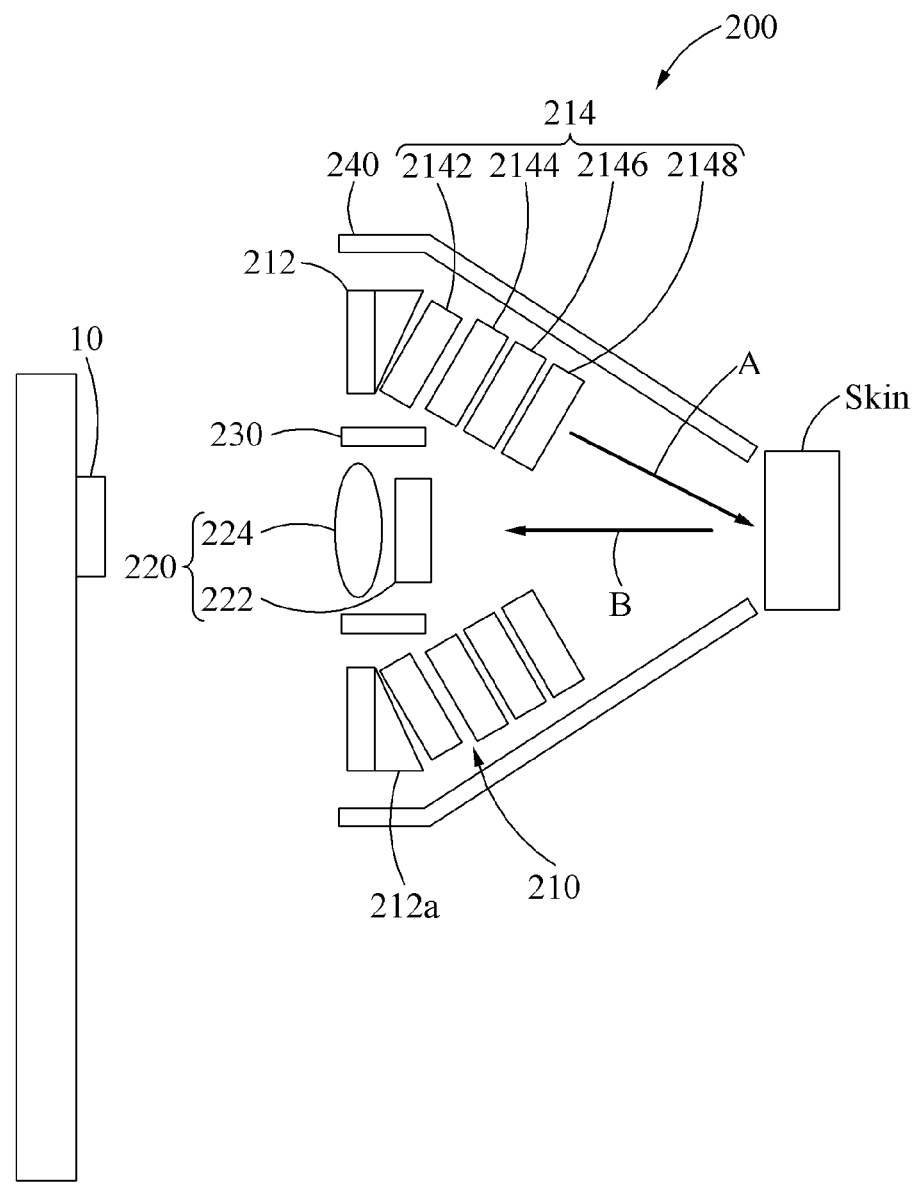
FIG. 5 is a diagram illustrating a multispectral imaging device according to an example embodiment.
Figure 6:
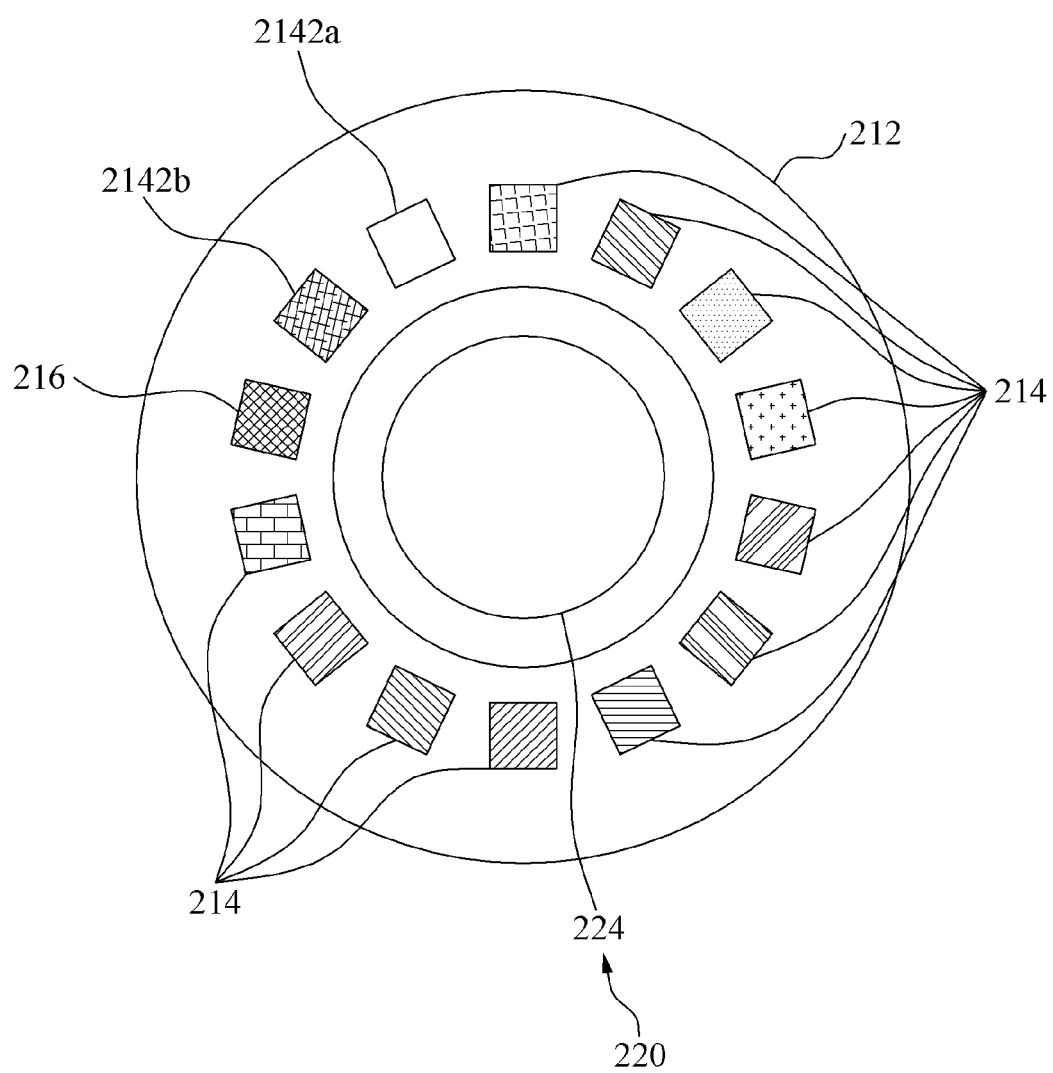
FIG. 6 is a diagram illustrating an illuminator.

FIG. 5 is a diagram illustrating a multispectral imaging device according to an example embodiment, and FIG. 6 is a diagram illustrating an illuminator.

Referring to FIG. 5, a multispectral imaging device 200 may include an illuminator 210, a detector 220, a shield 230, and a cover 240.

In the multispectral imaging device 200, the illuminator 210 and the detector 220 may disposed on the same axis. The illuminator 210 may include the detector 220. The shield 230 may be disposed on an outer side of the detector 220. The cover 240 may be disposed on an outer side of the illuminator 210.

The illuminator 210 may emit an LED light for skin illumination. The illuminator 210 may include an LED substrate 212 and a plurality of LED modules 214 attached on the LED substrate 212.

The LED substrate 212 may have an inclined face 212a in one face facing the skin. The inclined face 212a may be formed on the one face of the LED substrate 212 to be inclined toward the skin.

The plurality of LED modules 214 may be attached on the inclined face 212a. Through this, the LED light emitted from the plurality of LED modules 214 may be slantly transferred in an inclination direction of the inclined face 212a. For example, the LED light emitted from the plurality of LED modules 214 may be transferred to a point on the same axis of the illuminator 210 and the detector 220 or a center axis of the illuminator 210, the detector 220, the shield 230, or the cover 240.

The plurality of LED modules 214 may include a plurality of LED light sources 2142, a plurality of band-pass filters 2144, a diffusion plate 2146, and a first polarizing plate 2148.

The plurality of LED light sources 2142 may include a plurality of white light LEDs, an infrared LED, and a UV LED. In this example, the plurality of white light LEDs may be replaced with a plurality of LEDs emitting LED light having different wavelengths, and the wavelengths of the LED light emitted from the plurality of LEDs may correspond to a center wavelength of the plurality of band-pass filters 2144 attached to the plurality of LEDs.

Also, the plurality of LED light sources 2142 may be arranged to be inclined with respect to the same axis by the inclined face 212a of the LED substrate 212.

Referring to FIG. 6, the plurality of LED light sources 2142 may be radially arranged at preset intervals on the LED substrate 212 in a ring shape. For example, the plurality of LED light sources 2142 may be spaced at the same angle on the LED substrate 212.

The plurality of band-pass filters 2144 may be provided to be in contact with at least a portion of the plurality of LEDs or the plurality of LED light sources 2142.

Because the plurality of LED light sources 2142 has a relatively large bandwidth, the plurality of band-pass filters 2144 may be implemented as a filter with a small bandwidth, thereby increasing a spectral imaging performance.

For example, the plurality of band-pass filters 2144 may not be in contact with a portion of the plurality of LEDs so that white light is emitted from a white light LED 2142a as indicated by an empty block in FIG. 6. Also, the plurality of band-pass filters 2144 may not be in contact with an infrared LED 2142b and a UV LED (not shown).

An image spectral index or strength acquired from the camera 10 using the white light emitted from the white light LED 2142a may be used to determine a correction factor when correcting a spectral image.

The plurality of band-pass filters 2144 may be arranged to be inclined with respect to the same axis by the inclined face 212a of the LED substrate 212.

The plurality of LED light sources 2142 arranged to be in contact with the plurality of band-pass filters 2144 may emit light having different center wavelengths.

For example, when a number of the plurality of band-pass filters 2144 is nine, light corresponding to nine wavelengths of 435 nm, 453 nm, 493 nm, 520 nm, 545 nm, 580 nm, 605 nm, 638 nm, and 663 nm may be emitted. The number of the plurality of band-pass filters 2144 is not limited thereto, and the number of the plurality of band-pass filters 2144 may be more than nine or less than nine depending on an example.

The diffusion plate 2146 may be disposed to be in contact with the plurality of band-pass filters 2144 in a direction in which the LED light travels. In this instance, the diffusion plate 2146 may be arranged to be inclined with respect to the same axis by the inclined face 212a of the LED substrate 212.

Specifically, the diffusion plate 2146 may be implemented as a plurality of diffusion plates arranged to be in contact with the plurality of band-pass filters 2144. Also, the diffusion plate 2146 itself may be provided in the ring shape.

Using the diffusion plate 2146, the LED light having passed the plurality of band-pass filters 2144 may be evenly diffused so as to be applied to a wide area on the skin.

The first polarizing plate 2148 may be disposed to be in contact with the diffusion plate 2146 in a direction in which the LED light travels. In this instance, the first polarizing plate 2148 may be arranged to be inclined with respect to the same axis by the inclined face 212a of the LED substrate 212.

The first polarizing plate 2148 may be a vertical polarizing plate that polarizes the LED light in a first direction, for example, a vertical direction. By using the vertical polarizing plate, straightness or transparency may be improved so that light is transmitted deep into the skin.

The first polarizing plate 2148 may also be implemented as a horizontal polarizing plate, and any directional polarizing plate orthogonal to a second polarizing plate 222 of the detector 220 may be applicable.

The first polarizing plate 2148 may be implemented as a plurality of polarizing plates, each arranged to be in contact with the diffusion plate 2146. Also, the first polarizing plate 2148 itself may be provided in the ring shape.

As illustrated in FIG. 6, the plurality of LED modules 214 may be attached on the LED substrate 212 such that the plurality of LED modules 214 is easily attached to or detached from the LED substrate 212.

A light detector 216 may also be attached on the LED substrate 212. For example, the light detector 216 may be used for measuring an impedance of the skin. The light detector 216 may detect an optical signal and change the optical signal to an electrical signal. The light detector 216 may detect an infrared ray emitted from the infrared LED 2142b and change the infrared ray to an electrical signal, or detect an infrared ray reflected from the skin and change the infrared ray to an electrical signal. In this case, the multispectral imaging device 200 may acquire a spectral image of the skin and also measure a hydration of the skin.

The infrared LED 2142b and the light detector 216 may be disposed adjacent to each other or disposed facing each other on the LED substrate 212.

Referring back to FIG. 5, the detector 220 may be disposed in the illuminator 210.

The detector 220 may allow light scattered on the skin to be incident on the camera 10. The detector 220 may include the second polarizing plate 222 and an optical lens 224.

In this example, a path A of the LED light emitted from the illuminator 210 may be formed to be inclined toward the skin. Also, a path B of the light reflected or scattered by the skin may be formed on the same axis on which the illuminator 210 and the detector 220 are arranged. The path A of the LED light emitted from the illuminator 210 may be formed externally to the detector 220. The path B of the light reflected or scattered by the skin may be formed internally to the detector 220. As such, the path A of the LED light emitted from the illuminator 210 and the path B of the light reflected or scattered by the skin may be formed differently.

The second polarizing plate 222 may polarize the light reflected or scattered by the skin in a second direction. In this example, the second direction may be a direction orthogonal to the first direction of the first polarizing plate 2148, for example, a horizontal direction.

As such, the second polarizing plate 222 may polarize the light reflected or scattered by the skin in the direction orthogonal to the first direction of the first polarizing plate 2148, whereby the light reflected from the skin is prevented from being incident on the camera 10.

For example, when the LED light is incident on the skin, a portion of the LED light may penetrate into the skin to be scattered after interaction with the skin, or a portion of the LED light may be reflected directly without interacting with the skin.

In this example, when the LED light penetrates into the skin and interacts with the skin, the LED light may lose a polarization. In contrast, when the LED light is reflected without interacting with the skin, the polarization of the LED light may be maintained. Thus, when the second polarizing plate 222 polarizes the light in the direction orthogonal to the first direction of the first polarizing plate 2148, the light reflected without interacting with the skin may not pass through the second polarizing plate 222. In other words, the light reflected without interacting with the skin may not be incident on the camera 10, and the light penetrating into the skin and interacting with the skin may be effectively incident on the camera 10.

Also, the optical lens 224 may be disposed in a direction in which the light reflected or scattered by the skin travels from the second polarizing plate 222.

For example, the skin, the second polarizing plate 222, the optical lens 224, and the camera 10 may be on a line extending from the path B of the light reflected or scattered by the skin.

The optical lens 224 may refract the light polarized by the second polarizing plate 222, for example, the light penetrating into the skin and interacting with the skin or the light scattered on the skin. The light scattered on the skin may be effectively incident on the camera 10.

Through this, the camera 10 may acquire a multispectral image of the skin.

Although FIG. 5 illustrates the camera 10 is separate from the multispectral imaging device 200, a configuration of the camera 10 is not limited thereto.

In one example, the camera 10 may be attached on an opposite side of the multispectral imaging device 200 to a side facing the skin. Also, the camera 10 may be a portion of the multispectral imaging device 200.

In another example, the camera 10 may be attached to the mobile device such as a smartphone. When the multispectral imaging device 200 is attached to the mobile device, an image acquired by the camera 10 may be shown in the mobile device.

In another example, the camera 10 may be, for example, a complementary metal-oxide semiconductor (CMOS) camera. In this example, the multispectral imaging device 200 may be attached to the CMOS camera and the camera 10 may be wired or wirelessly connected to the mobile device. As such, the camera 10 may be provided in various configurations.

The shield 230 may be between the illuminator 210 and the detector 220.

The shield 230 may be formed in a cylindrical shape to internally receive the detector 220. The second polarizing plate 222 and the optical lens 224 may be disposed inside the shield 230. A shape of the shield 230 is not limited to the cylindrical shape and any shape that allows the detector 220 to be accommodated inside may be applicable.

The illuminator 210 may be disposed externally to the shield 230.

Although FIG. 5 illustrates an enlarged view of the LED substrate 212 and the LED module 214 so that the LED module 214 appears to be positioned closer to the skin than the shield 230, the LED substrate 212 and the LED module 214 may be arranged on an outer side of the shield 230.

The shield 230 may prevent the LED light diffused by the diffusion plate 2146 from being introduced to the path B of the light reflected or scattered by the skin. Thus, the LED light diffused by the diffusion plate 2146 may travel toward the skin through the path A of the LED light emitted from the illuminator 210. As such, light other than the light scattered on the skin by passing the detector 220 may not be incident on the camera 10 and thus, noise may be reduced.

The cover 240 may accommodate the illuminator 210 and the detector 220.

The detector 220 may be disposed on a center axis of the cover 240 and the illuminator 210 may be disposed to be spaced apart in a radial direction from the center axis of the cover 240. Thus, based on the center axis of the cover 240, the detector 220 may be disposed internally and the illuminator 210 may be disposed externally.

In this example, one end of the cover 240 may be adjacent to the camera 10, and the other end of the cover 240 may be adjacent to the skin.

The cover 240 may have a cross-sectional area decreasing from the one end toward the other end. Such shape of the cover 240 may affect the path A of the LED light emitted from the illuminator 210 so that the LED light emitted from the illuminator 210 is concentrated onto the skin.

The illuminator 210, the detector 220, and the shield 230 may be disposed in an inner space adjacent to the one end of the cover 240 and a cross-sectional area corresponding to the inner space of the cover 240 may not be changed. A cross-sectional area corresponding to a portion of the cover 240 including the path A of the LED light emitted from the illuminator 210 and the path B of the light reflected or scattered by the skin may decrease.

The cover 240 may be, for example, a light-hermetic enclosure that allows the illuminator 210 and the detector 220 to be disposed in a dark room. In this example, the cover 240 may block external light such that the camera 10 acquires an image with increased clarity.

Hereinafter, a method of acquiring an image using a multispectral imaging device will be described.

Figure 7:
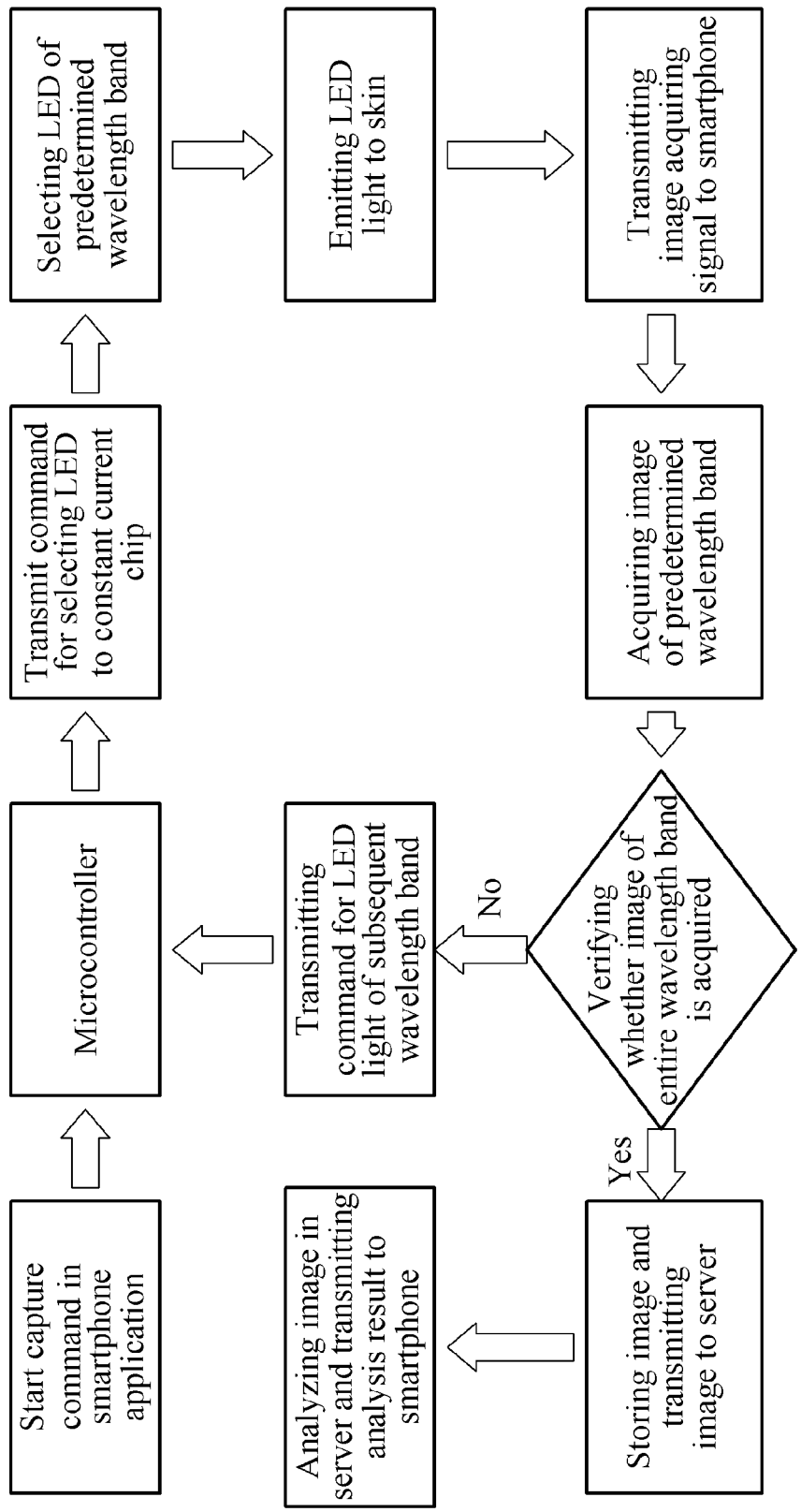
FIG. 7 is a flowchart illustrating a method of acquiring an image using a multispectral imaging device according to an example embodiment.
Figure 8:
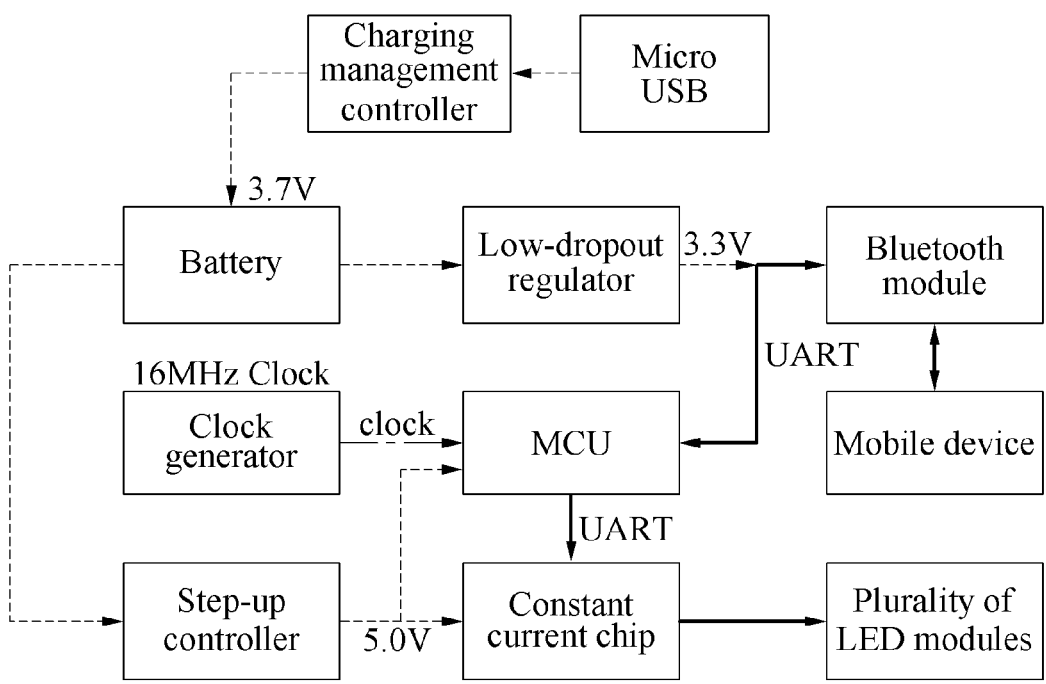
FIG. 8 is a diagram illustrating an interface circuit for acquiring an image using a multispectral imaging device according to an example embodiment.

FIG. 7 is a flowchart illustrating a method of acquiring an image using a multispectral imaging device according to an example embodiment, and FIG. 8 is a diagram illustrating an interface circuit for acquiring an image using a multispectral imaging device according to an example embodiment.

The following description will be provided based on an example in which a multispectral imaging device is attached to, for example, a CMOS camera and the CMOS camera is connected to a smartphone.

Referring to FIG. 7, a start capture command may be delivered from a smartphone application to a microcontroller through, for example, Bluetooth. The microcontroller may transmit a command to a constant current chip for selecting an LED from a plurality of LED light sources.

Thereafter, an LED of a predetermined wavelength band may be selected from the plurality of LED light sources.

Specifically, since the plurality of LED light sources is arranged to be in contact with a plurality of band-pass filters, selecting the LED of the predetermined wavelength band may indicate that an LED light source and a filter of the predetermined wavelength band among the plurality of band-pass filters are combined.

Thus, when a predetermined LED light source is lighted on, the LED light source may pass the filter of the predetermined wavelength band so that an LED light of the predetermined wavelength band is emitted.

The LED light emitted from the LED light source may be scattered or reflected by the skin to be incident on the CMOS camera through the multispectral imaging device. The light incident on the CMOS camera may form an image and transmit an image acquiring signal to the smartphone through, for example, the Bluetooth. Through this, the smartphone may acquire the image of the predetermined wavelength band.

The smartphone may verify whether an image of the entire wavelength band is acquired. When the image of the entire wavelength band is not acquired, a command for an LED light of a subsequent wavelength band may be transmitted to the microcontroller and the microcontroller may transmit a command to the constant current chip for selecting an LED from the plurality of LED light sources.

Subsequently, an LED of a predetermined wavelength band for which an image has not been acquired may be selected from the plurality of LED light sources.

Specifically, since the plurality of LED light sources is arranged to be in contact with the plurality of band-pass filters, selecting the LED of the predetermined wavelength band for which an image has not been acquired may indicate that an LED light source and a filter of the predetermined wavelength band among the plurality of band-pass filters are combined.

Thus, when a predetermined LED light source is lighted on, the predetermined LED light source may pass the filter of the predetermined wavelength band so that an LED light of the predetermined wavelength band is emitted.

Through such process, the smartphone may verify whether the image for the entire wavelength band is acquire. When the image for the entire wavelength band is acquired, the image may be stored and transmitted to a server, for example, a spectral image processing server. The image transmitted to the server may be analyzed, so that an image analysis image is transmitted to the smartphone.

As such, while the LED of the predetermined wavelength band is lighted on, the CMOS camera may simultaneously acquire or record an image. Such process may be repeated to acquire images at consecutive wavelengths for multispectral imaging and analysis.

The smartphone and the multispectral imaging device may be connected for synchronization by an interface circuit. The interface circuit may be embedded in the multispectral imaging device.

The interface circuit may include a microcontroller unit (MCU), a Bluetooth module, a constant current chip for an LED, a step-up controller, a low-dropout regulator, and a clock generator.

The MCU may receive commands from the smartphone through the Bluetooth module and transfer the commands to the constant current chip to light on or off an LED of a predetermined wavelength selected from a plurality of LED light sources through universal asynchronous receiver/transmitter (UART) communication.

A lithium battery of, for example, 3.7 volts (V) may be used for power supply to the interface circuit. An input voltage of 3.7 V may be boosted to 5 V to drive both the MCU and the constant current chip, whereby the LED light is more stably emitted. The input voltage of 3.7 V may also be reduced to 3.3 V to supply power to the Bluetooth module.

The multispectral imaging device may acquire an image of a predetermined wavelength band by selectively lighting on or off an LED light source without need to rotate an LED substrate. Also, the multispectral imaging device may acquire an image with increased clarity by blocking external light and light reflected from the skin without interacting with the skin.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The invention claimed is:

1. A multispectral imaging device comprising:
   an illuminator configured to emit light emitting diode (LED) light for skin illumination to a skin; and
   a detector configured to allow light reflected from the skin to be incident on a camera,
   wherein the illuminator is disposed on an outer side of the detector such that a path of the LED light emitted from the illuminator is formed externally to the detector and a path of the light reflected from the skin is formed internally to the detector,
   wherein the illuminator comprises:
      an LED substrate on which a plurality of LED light sources is mounted; and
      a plurality of band-pass filters provided to be in contact with at least a portion of the plurality of LED light sources,
   wherein the LED substrate is in a ring shape, and
   wherein the plurality of LED light sources and the plurality of band-pass filters are selectively activated by controlling the plurality of LED light sources to be on or off, and the plurality of LED light sources is controlled to be on or off by an embedded system controlled by a mobile device.

2. The multispectral imaging device of claim 1, wherein the detector comprises:
   an optical lens configured to refract the light reflected from the skin; and
   a first polarizing plate configured to polarize the light refracted by the optical lens in a first direction, and
   wherein the camera is disposed on a center axis of the first polarizing plate and the optical lens.

3. The multispectral imaging device of claim 2, wherein the detector further comprises:
   a shield configured to internally receive the optical lens and the first polarizing plate, and
   wherein the illuminator is disposed on an outer side of the shield.

4. The multispectral imaging device of claim 1, wherein the plurality of LED light sources includes one ultraviolet (UV) LED, one near infrared (NIR) LED, and a plurality of white LEDs or a plurality of LEDs having different wavelengths corresponding to a center wavelength of the plurality of band-pass filters, and
   wherein the plurality of band-pass filters is arranged to be in contact with the plurality of white LEDs or the plurality of LEDs.

5. The multispectral imaging device of claim 4, wherein a number of the band-pass filters is less than a number of the white LEDs by one.

6. The multispectral imaging device of claim 1, further comprising:
   a cover configured to internally receive the illuminator and the detector, wherein the cover allows the illuminator and the detector to be disposed in a darkroom such that an external light influence corresponding to the light reflected from the skin or the LED light emitted from the illuminator is blocked.

7. The multispectral imaging device of claim 6, wherein the cover comprises: a connecting member used for attachment to a mobile device, and
   wherein the connecting member is adjustable in length.

8. A multispectral imaging device comprising:
   an illuminator configured to emit light emitting diode (LED) light for skin illumination to a skin; and
   a detector configured to allow light reflected from the skin to be incident on a camera,
   wherein the illuminator is disposed on an outer side of the detector such that a path of the LED light emitted from the illuminator is formed externally to the detector and a path of the light reflected from the skin is formed internally to the detector,
   wherein the illuminator comprises:
      an LED substrate on which a plurality of LED light sources is mounted; and
      a plurality of band-pass filters provided to be in contact with at least a portion of the plurality of LED light sources,
   wherein the LED substrate is in a ring shape,
   wherein the illuminator further comprises: a diffusion plate disposed to be in contact with the plurality of band-pass filters in a direction in which the LED light is promoted, to diffuse the LED light, and
   wherein the diffusion plate includes a diffuser configured to diffuse light in a same shape as a shape that the plurality of LED light sources is mounted.

9. The multispectral imaging device of claim 8, wherein the illuminator further comprises: a second polarizing plate disposed to be in contact with the diffusion plate in the direction in which the LED light is promoted, to polarize the LED light diffused by the diffusion plate in a second direction, and wherein the second polarizing plate includes a polarizer in a same shape as the diffuser.

10. A multispectral imaging device comprising:
an illuminator configured to emit light emitting diode (LED) light for skin illumination to a skin; and
a detector configured to allow light scattered on the skin to be incident on a camera,
wherein the illuminator and the detector are arranged on a same axis, a path of the LED light emitted from the illuminator is formed to be inclined toward the skin, and a path of the light scattered or reflected by the skin is formed on the same axis,
wherein the illuminator comprises:
an LED substrate on which a plurality of LED light sources is mounted; and
a plurality of band-pass filters provided to be in contact with at least a portion of the plurality of LED light sources,
wherein the LED substrate includes an inclined plane formed to be inclined toward the skin, and wherein the plurality of LED light sources is mounted on the inclined plane, and
wherein the plurality of LED light sources and the plurality of band-pass filters are selectively connected by controlling the plurality of LED light sources to be on or off, and the plurality of LED light sources is controlled to be on or off by an embedded system controlled by a mobile device.

11. The multispectral imaging device of claim 10, wherein the illuminator further comprises:
a diffusion plate disposed to be in contact with the plurality of band-pass filters in a direction in which the LED light is promoted, to diffuse the LED light; and
a first polarizing plate disposed to be in contact with the diffusion plate in the direction in which the LED light is promoted, to polarize the LED light diffused by the diffusion plate in a first direction.

12. The multispectral imaging device of claim 11, further comprising:
a shield provided in a cylindrical shape to internally receive the detector,
wherein the shield is configured to prevent the LED light diffused by the diffusion plate from being introduced to the path of the light scattered or reflected by the skin.

13. The multispectral imaging device of claim 11,
wherein the detector comprises: a second polarizing plane configured to polarize the light scattered or reflected by the skin in a second direction orthogonal to the first direction, and
wherein the second polarizing plate is configured to prevent light reflected from the skin from being incident on the camera.

14. The multispectral imaging device of claim 13,
wherein the detector further comprises: an optical lens configured to refract the light polarized by the second polarizing plate; and
wherein the skin, the second polarizing plate, the optical lens, and the camera are on a same line.

15. The multispectral imaging device of claim 10, wherein the LED substrate is in a ring shape, the detector is disposed to penetrate the LED substrate, and the plurality of LED light sources is radially arranged on the LED substrate at intervals.

16. The multispectral imaging device of claim 10, further comprising:
a cover configured to internally receive the illuminator and the detector,
wherein the detector is disposed on a center axis of the cover and the illuminator is spaced apart from the center axis in a radial direction.

17. The multispectral imaging device of claim 16, wherein one end of the cover is disposed adjacent to the camera, the other end of the cover is disposed adjacent to the skin, and the cover has a cross-sectional area that decreases from one end toward the other end.

* * * * *